United States Patent
Watanabe (10) Patent No.: US 7,213,462 B2
(45) Date of Patent: May 8, 2007

(54) HUMIDITY SENSOR AND COMPOSITE SENSOR HAVING HUMIDITY DETECTING FUNCTION

(75) Inventor: Yoshifumi Watanabe, Kariya (JP)

(73) Assignee: Denso Corporation, Kariya (JP)

( * ) Notice: Subject to any disclaimer, the term of this patent is extended or adjusted under 35 U.S.C. 154(b) by 43 days.

(21) Appl. No.: 11/199,228

(22) Filed: Aug. 9, 2005

(65) Prior Publication Data
US 2006/0037404 A1 Feb. 23, 2006

(30) Foreign Application Priority Data
Aug. 20, 2004 (JP) .............................. 2004-240310

(51) Int. Cl.
*G01F 7/00* (2006.01)
(52) U.S. Cl. ....................................................... 73/714
(58) Field of Classification Search ............. 73/335.04, 73/29.05, 336.5, 335.6, 714; 361/286, 323
See application file for complete search history.

(56) References Cited

U.S. PATENT DOCUMENTS 4,263,576 A * 4/1981 Murata et al. ................. 338/35
4,429,343 A * 1/1984 Freud ........................ 361/286
5,177,662 A * 1/1993 Thoma ....................... 361/286
6,742,387 B2 * 6/2004 Hamamoto et al. ...... 73/335.04

* cited by examiner

Primary Examiner—Jewel V. Thompson
(74) Attorney, Agent, or Firm—Posz Law Group, PLC

(57) ABSTRACT

A humidity sensor includes a resin molding body having a wall portion as a barrage, a chip having at least a humidity sensing function and fixed to a portion of the resin molding body inside the wall portion, and a terminal conductor insert-molded in the resin molding body and partially leaded to an exterior of the resin molding body. Here, the terminal conductor is electrically connected to the chip inside the wall portion of the resin molding body. In the humidity sensor, a protecting material having a humidity sensing property is filled in the wall portion and covers an entire electric connecting portion of the chip and the terminal conductor. The structure of the humidity sensor can be suitably used for a composite sensor including a chip having a humidity sensing function.

27 Claims, 8 Drawing Sheets

HUMIDITY SENSOR AND COMPOSITE SENSOR HAVING HUMIDITY DETECTING FUNCTION

CROSS REFERENCE TO RELATED APPLICATION

This application is based on Japanese Patent Application No. 2004-240310 filed on Aug. 20, 2004, the contents of which are incorporated herein by reference in its entirety.

FIELD OF THE INVENTION

The present invention relates to a humidity sensor and a composite sensor having a humidity detecting function (structure).

BACKGROUND OF THE INVENTION

For example, a capacitance-changing type humidity sensor is described in U.S. Pat. No. 6,742,387 (corresponding to JP-A-2003-156464). This humidity sensor is used for detecting humidity within a room to perform humidity control of an air conditioner, or is used for detecting humidity of the outdoors to make a weather observation.

When it is simply called humidity, there is generally relative humidity and absolute humidity. In the relative humidity, the ratio of an amount of water vapor actually included within the atmosphere, to a maximum amount of water vapor (saturated water vapor pressure) able to be included in the atmosphere at its temperature, is shown by percentage. In the absolute humidity, the amount of water vapor included within the air of one cubic meter at one atmospheric pressure is shown by a gram number. The humidity sensor described here is normally used as a sensor for measuring the above-described relative humidity.

In this humidity sensor, for example, a silicon oxide film as an insulating film is formed on a silicon substrate. A pair of electrodes each of which has a comb teeth shape is formed on the silicon oxide film so as to be separated and opposed to each other on the same surface. A silicon nitride film as a protecting film is formed on this pair of electrodes. A humidity sensing film having a capacitance value changed in accordance with humidity is formed on the silicon nitride film so as to cover both the electrodes.

Here, an area for forming the humidity sensing film is constructed as a humidity sensing portion for sensing humidity. When moisture enters the interior of the humidity sensing film, the dielectric constant of the humidity sensing film is greatly changed in accordance with the entering moisture amount because the dielectric constant of a water molecule is large. As a result, the capacitance value between both the electrodes is also changed. In the humidity sensing portion, because the capacitance value between the pair of electrodes is changed in accordance with the humidity change around the sensor, humidity can be detected on the basis of this capacitance value change.

As mentioned above, in the humidity sensor for detecting the indoor humidity as a sensor for the humidity control of the air conditioner, or used for detecting the outdoor humidity for the weather observation, etc., the humidity can be appropriately detected on the basis of the dielectric constant change of the humidity sensing film, i.e., the capacitance value change between the pair of electrodes.

On the other hand, in recent years, it is desired to more accurately measure an intake air amount supplied to an engine so as to optimize an air-fuel ratio in electronic control fuel injection of the engine. As a method for measuring such an intake air amount, there are a mass flow system (L-EFI) for directly measuring the intake air amount by using e.g., an air flow meter, and a speed density system (D-EFI) for combining a pressure sensor and a temperature sensor and presuming the air amount supplied to the engine per one cycle by an engine rotation number and an intake pipe pressure. However, in each of these systems, because no water vapor included within the air can be separated from the air, its unseparated amount becomes an error. Accordingly, a method for detecting the humidity together with the intake air amount and more accurately measuring the air amount by this humidity detection is considered to aim at the engine control of higher precision in the future.

However, when the humidity sensor is arranged in an intake gas system of the engine, e.g., within an intake manifold, etc. so as to accurately measure the intake air amount in this way, the following disadvantages newly become matters unable to be neglected. That is, the interior of such an intake manifold lies under a deteriorated environment in which various polluting substances such as engine oil, carbon, fuel, etc. exist. Accordingly, when the humidity sensor is arranged under such an environment, there is a fear that such polluting substances are attached to the humidity sensing portion of the humidity sensor. If such polluting substances are attached to the humidity sensing portion, the flow of the moisture through the humidity sensing film is obstructed. Therefore, responsibility of the humidity sensor is extremely reduced. Further, because no dielectric constant of the polluting substance can be distinguished from that of the humidity sensing film, a shift is caused with respect to a measuring value of the humidity sensor.

Such a problem is also caused in a composite sensor considered to be particularly useful in the speed density system (D-EFI) and having a humidity detecting function provided by combining e.g., a pressure sensor, a temperature sensor, etc. with the humidity sensor.

SUMMARY OF THE INVENTION

In view of the above-described problems, it is an object of the present invention to provide a humidity sensor able to detect humidity with high precision even when the humidity sensor is arranged under a deteriorated environment such as an intake gas system of an engine, etc.

It is another object of the present invention to provide a composite sensor which includes a chip having a humidity detecting function.

According to an embodiment of the present invention, a humidity sensor includes a resin molding body having a wall portion as a barrage, a chip member having at least a humidity sensing function, which adheres and is fixed to a portion of the resin molding body inside the wall portion, and a terminal conductor insert-molded in the resin molding body and partially leaded to an exterior of the resin molding body. Here, the terminal conductor is electrically connected to the chip member inside the wall portion of the resin molding body. In the humidity sensor, a protecting material having a humidity sensing property is filled in the wall portion and covers an entire electric connecting portion of the chip member and the terminal conductor.

Accordingly, the surface area of the filled protecting material having the humidity sensing property is greatly widened. Therefore, as long as no polluting substance perfectly covers the surface of the filled protecting material having the humidity sensing property even when the above-mentioned polluting substance is attached to this humidity sensor, moisture enters from a portion except for this covering portion through this protecting material of the humidity sensing property. Thus, no function as this humidity sensor is damaged. That is, a resisting amount with respect to the attachment of the polluting substance is greatly improved by such a difference in the surface area. Further, the distances between the surface of the protecting material having the humidity sensing property and the pair of electrodes of a chip itself functioning as the humidity sensor are held to be sufficiently long by the filling of the protecting material having the humidity sensing property. Therefore, even when the dielectric constant of the attached polluting substance is high, there is no an influence in the electrical capacitance between these electrodes. The dielectric constant of the filled protecting material having the humidity sensing property is also really changed by humidity absorption, but such a change of the dielectric constant can be grasped as an experience value (experimental value) in advance. Accordingly, this changing amount is easily canceled by subsequent electric processing.

For example, the chip member can be constructed with one of a single chip that is formed by integrally integrating a humidity sensing portion having the humidity sensing function and a processing circuit for electrically processing humidity information from the humidity sensing portion, and a plurality of chips formed by separately integrating a chip having the humidity sensing portion and a processing circuit chip for electrically processing humidity information from the chip having the humidity sensing portion.

Alternatively, the chip member can be constructed with a plurality of chips functioning as the humidity sensing portion, and a processing circuit chip for electrically synthesis-processing humidity information from each of the chips. In this case, the chips functioning as the humidity sensing portion can be integrated separately from the processing circuit chip. Furthermore, the chips functioning as the humidity sensing portion can be constructed with odd chips of three or more than three, and the processing circuit chip processes the humidity information using signals from the chips by a majority decision.

Furthermore, the protecting material can cover all of the chip member and the electric connecting portion.

According to another embodiment of the present invention, a humidity sensor includes a resin molding body having a wall portion as a barrage, a chip having at least a humidity sensing function, and a processing circuit chip for electrically processing humidity information from the chip having the humidity sensing function. Here, the processing circuit chip adheres and is fixed to a portion of the resin molding body inside the wall portion. Further, a terminal conductor is insert-molded in the resin molding body and partially leaded to an exterior of the resin molding body, and the terminal conductor is electrically connected to the processing circuit chip inside the wall portion of the resin molding body. In the humidity sensor, a protecting material having a humidity sensing property is filled in the wall portion and covers an entire electric connecting portion of the processing circuit chip and the terminal conductor, the chip having the humidity sensing function is constructed with a flip chip having a metallic bump and has a humidity sensing portion arranged on an arrangement surface where the metallic bump is provided, and the chip having the humidity sensing function is electrically connected to the processing circuit chip by the metallic bump and is attached to the processing circuit chip through the electrical connection. In this case, the chip having the humidity sensing function can be effectively protected.

For example, a shield plate can cover the chip having the humidity sensing function and a circumference of the chip, on a surface opposite to the arrangement surface of the chip having the humidity sensing function. Further, the protecting material filled in the wall portion can cover an entire area including the chip having the humidity sensing function, the processing circuit chip, and the electric connecting portion of the chip having the humidity sensing function and the processing circuit chip.

According to another embodiment of the present invention, a composite sensor includes a resin molding body having a wall portion as a barrage, a chip member having at least a humidity sensing function and a pressure sensing function, which is fixed to a portion of the resin molding body inside the wall portion, and a terminal conductor insert-molded in the resin molding body and partially leaded to an exterior of the resin molding body. Here, the terminal conductor is electrically connected to the chip member inside the wall portion of the resin molding body, and a protecting material having a humidity sensing property and a pressure sensing property is filled in the wall portion and covers an entire electric connecting portion of the chip member and the terminal conductor.

Accordingly, the surface area of the filled protecting material of the humidity sensing property is greatly widened. Therefore, as long as no polluting substance perfectly covers the surface of the filled protecting material of the humidity sensing property even when a polluting substance is attached to this composite sensor, moisture enters from a portion except for this covering portion through this protecting material of the humidity sensing property. Thus, no function as this humidity sensor is damaged. That is, a resisting amount with respect to the attachment of the polluting substance is greatly improved.

For example, the chip member can be constructed with a single chip that is formed by integrally integrating a humidity sensing portion having the humidity sensing function, a pressure sensing portion having the pressure sensing function, and a processing circuit for electrically processing humidity information from the humidity sensing portion and pressure information from the pressure sensing portion.

Alternatively, the chip member can be constructed with a chip in which a humidity sensing portion having the humidity sensing function and a pressure sensing portion having the pressure sensing function are integrated, and a processing circuit chip for electrically processing information from the chip having the humidity sensing portion and the pressure sensing portion.

Furthermore, the chip member can be constructed with a chip having the humidity sensing function, and a processing circuit chip including a pressure sensing portion having the pressure sensing function. In this case, the processing circuit chip electrically processes information from the chip having the humidity sensing function and information from the pressure sensing portion.

Alternatively, the chip member can be constructed with a chip having the pressure sensing function, and a processing circuit chip including a humidity sensing portion having the humidity sensing function. In this case, the processing circuit chip electrically processes information from the chip having the pressure sensing function and information from the humidity sensing portion.

Furthermore, the chip member can be constructed with a chip having the humidity sensing function, a chip having the pressure sensing function, and a processing circuit chip for electrically processing information from the chip having the pressure sensing function and information from the chip having the humidity sensing function.

According to another embodiment of the present invention, a composite sensor includes a humidity chip having at least a humidity sensing function and fixed to a portion of the resin molding body inside the wall portion, a pressure chip having at least a pressure sensing function and fixed to a portion of the resin molding body inside the wall portion, and a terminal conductor insert-molded in the resin molding body and partially leaded to an exterior of the resin molding body. In the composite sensor, the terminal conductor is electrically connected to the humidity chip and the pressure chip inside the wall portion of the resin molding body, and a protecting material having a humidity sensing property and pressure sensing property is filled in the wall portion and covers an entire electric connecting portion of the chips and the terminal conductor. Furthermore, at least the humidity chip is provided independently and has a humidity sensing portion for detecting humidity, the humidity sensing portion of the humidity chip is enclosed by a separation wall that is higher than the wall portion of the resin molding body, and the separation wall selectively separates the humidity sensing portion from the protecting material filled in the wall portion of the resin molding body. Accordingly, the humidity sensing portion can accurately detect the humidity.

In this case, a protecting film, having a thickness thinner than the thickness of the protecting material, can be provided to cover the humidity sensing portion separated from the protecting material. Furthermore, a temperature detecting element can be located at an outer side of the wall portion of the resin molding body.

BRIEF DESCRIPTION OF THE DRAWINGS

The above and other objects, features and advantages of the present invention will become more apparent from the following detailed description of preferred embodiments made with reference to the accompanying drawings, in which.

DETAILED DESCRIPTION OF PREFERRED EMBODIMENTS

First Embodiment

The first embodiment and modifications thereof will be described with reference to FIG. 1A to FIG. 9.

Figure 1A:
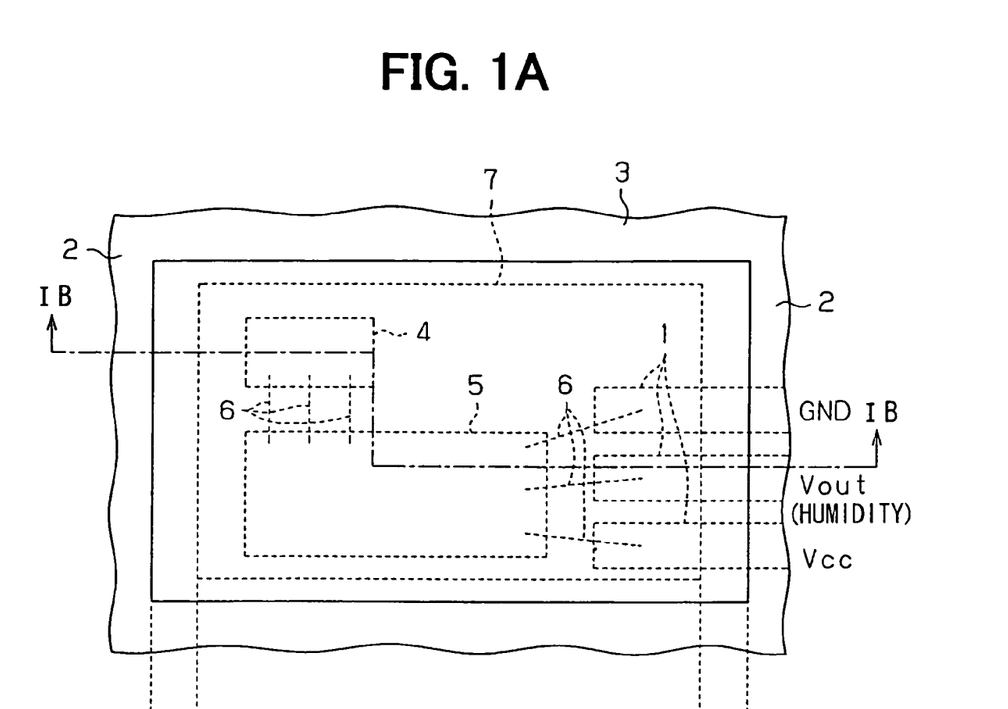
FIG. 1A is a plan view showing a humidity sensor according to a first embodiment of the present invention.
Figure 1B:
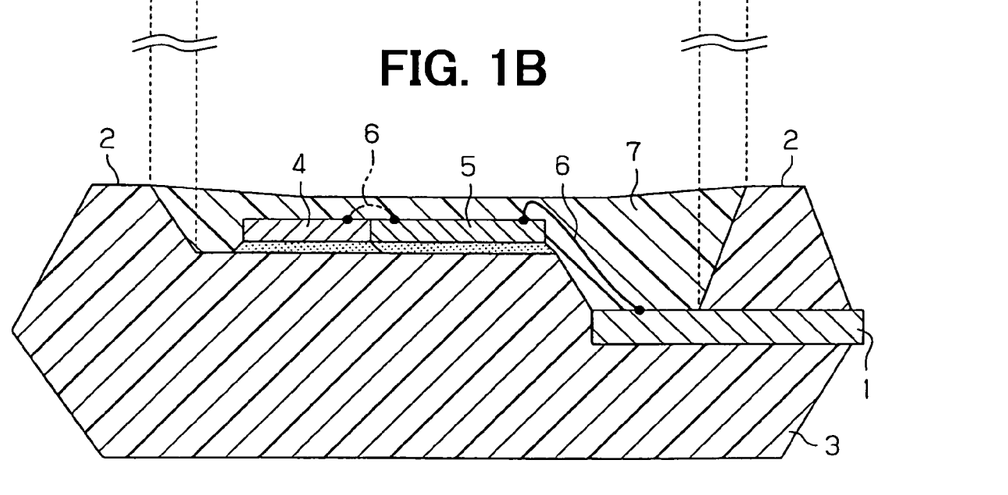
FIG. 1B is a cross-sectional view showing the humidity sensor taken along line IB—IB in FIG. 1A.

As shown in FIGS. 1A and 1B, a humidity sensor is insert-molded to a resin molding body 3 having a wall portion 2 as a barrage in the circumference such that conductors 1 (terminal conductor) as sensor terminals are partially guided to the exterior. A humidity sensor chip 4 functioning as the humidity sensor, and a processing circuit chip 5 for electrically processing humidity information obtained from the humidity sensor chip 4 are separately integrated, bonded and fixed to an intermediate portion of this resin molding body 3, i.e., inside the wall portion 2.

The bonded and fixed humidity sensor chip 4, the processing circuit chip 5 and the conductor 1 as the sensor terminals are electrically connected through bonding wires 6 inside the wall portion 2 of the resin molding body 3. The entire electric connecting portion including the bonding wires 6 is covered with a protecting material 7 having a humidity sensing property filled in the wall portion 2 as a barrage.

Next, the structure of the humidity sensor chip 4 adopted in this humidity sensor will be explained with reference to FIGS. 2 and 3.

Figure 2:
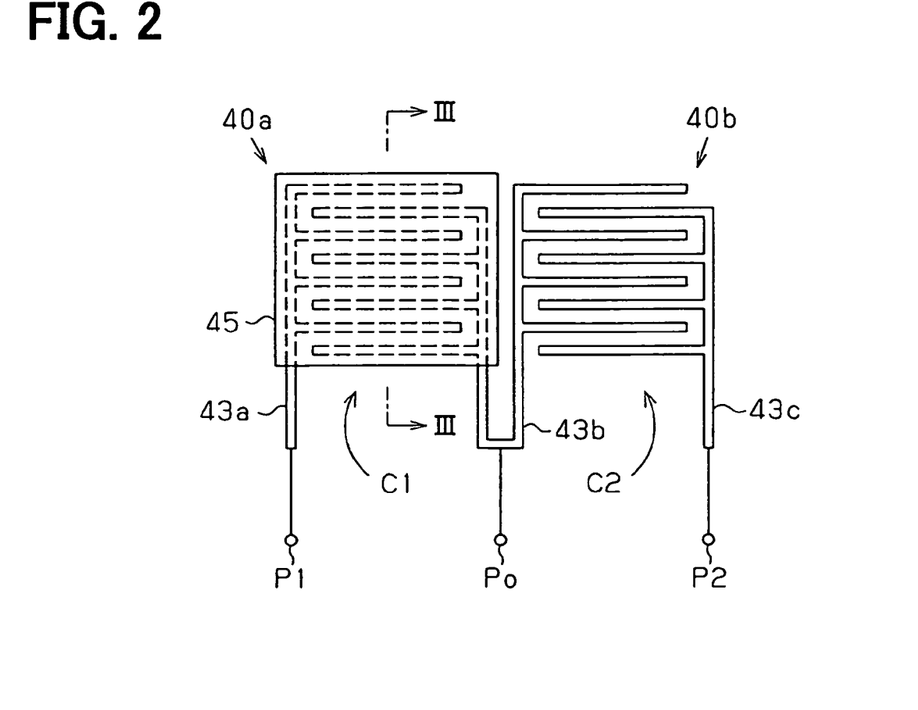
FIG. 2 is a plan view showing a humidity sensor chip of the humidity sensor according to the first embodiment.

As shown by the planar structure of the humidity sensor chip 4 in FIG. 2, this humidity sensor chip 4 is a humidity sensor of a so-called capacitance changing type, and is constructed with a humidity sensing portion 40a and a reference portion 40b. The humidity sensing portion 40a is constructed with comb teeth shaped electrodes (wiring) 43a, 43b insulated by a dielectric film, and a humidity sensing film 45 arranged for covering these electrodes 43a, 43b and the dielectric film. Similarly, the reference portion 40b is constructed with comb teeth shaped electrodes (wiring) 43b, 43c insulated by the dielectric film.

Figure 3:
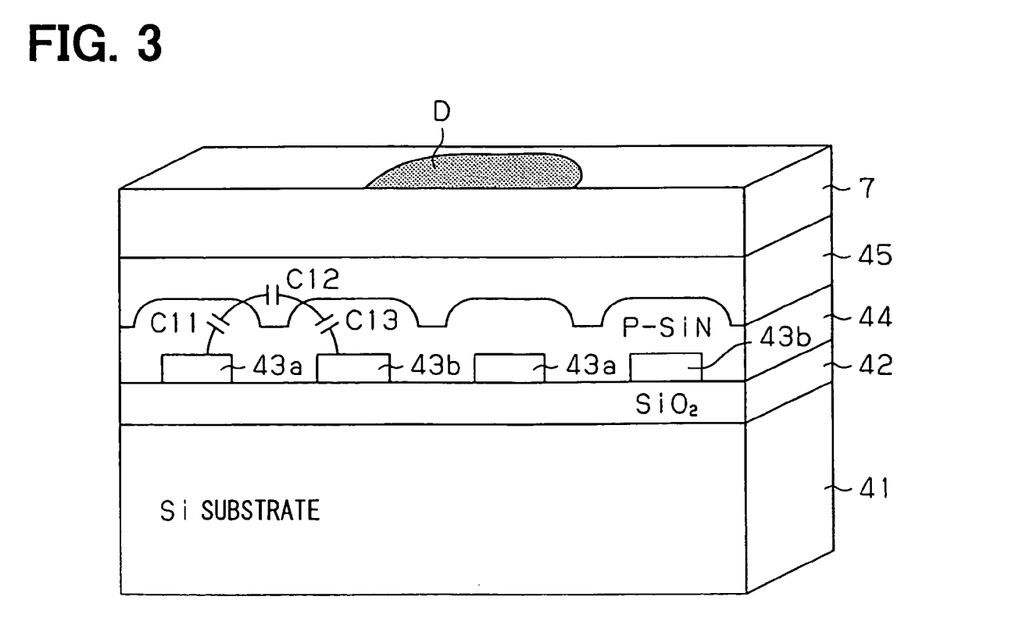
FIG. 3 is a perspective sectional view taken along line III—III in FIG. 2.

In the humidity sensing portion 40a, as shown in FIG. 3, for example, after an oxide film ($SiO_2$) 42 is formed on a Si substrate 41, the electrodes 43a, 43b are formed by using aluminum (Al), etc. Thereafter, a nitride film (P—SiN) 44 as the dielectric film is deposited and formed by the plasma CVD (chemical vapor deposition) method, for example. Thus, the portion between the electrodes 43a, 43b is insulated. Further, the humidity sensing film 45 made of polyimide, etc. is coated on this nitride film 44. In this embodiment, the upper portion of the humidity sensing film 45 is particularly formed in a shape covered with the protecting material 7 having the humidity sensing property. The protecting material 7 is made of gel of a fluorine material (e.g., fluoro silicon gel or fluorine gel), etc. FIG. 3 shows a situation in which a polluting substance D is attached to a part of the protecting material 7. For example, engine oil, carbon, fuel, etc. as this polluting substance D is attached to the protecting material 7 when the humidity sensing portion 40a is arranged under an environment in the interior of an intake manifold of an engine.

On the other hand, the illustration of a sectional structure of the reference portion 40b is omitted, but this sectional structure basically becomes a structure in which the humidity sensing film 45 is removed from the structure shown in FIG. 3 and the reference portion 40b is covered with a suitable film material of a non-humidity sensing property such as mold resin, etc. instead of the humidity sensing film 45. That is, only the humidity sensing portion 40a has the humidity sensing film 45, and is covered with the protecting material 7 having the humidity sensing property together with the film material of the non-humidity sensing property of the reference portion 40b. Further, in the humidity sensing portion 40a, its electrical capacitance C1 is calculated as the synthetic capacitance between the electrodes of the comb teeth shape. For example, as shown in FIG. 3, the electrical capacitance C1 is calculated as the synthetic capacitance of electrical capacitances C11 and C13 of the nitride film 44, and electrical capacitance C12 of the humidity sensing film 45. That is, when moisture in the atmosphere is attached to the protecting material 7 having the humidity sensing property, the dielectric constant of the humidity sensing portion 40a is changed and the value of the electrical capacitance C12 is changed. Thus, the entire synthetic capacitance (electrical capacitance) C1 is determined by adding the changing amount of the electrical capacitance C12.

The electrical capacitance C2 of the reference portion 40b is also calculated as the synthetic capacitance between the electrodes of the comb teeth shape. That is, although the illustration of this electrical capacitance C2 is omitted, this electrical capacitance C2 is calculated as the synthetic capacitance between the electrical capacitance of the nitride film as the dielectric film and the electrical capacitance of the upper portion of the nitride film. In this example, the reference portion 40b is set to a structure unexposed to the exterior. Therefore, the synthetic capacitance (electrical capacitance) C2 of the reference portion 40b always becomes a constant value without being influenced by the humidity within the atmosphere, etc.

Next, one example of the electric construction of this humidity sensor will be explained with reference to FIG. 4.

Figure 4:
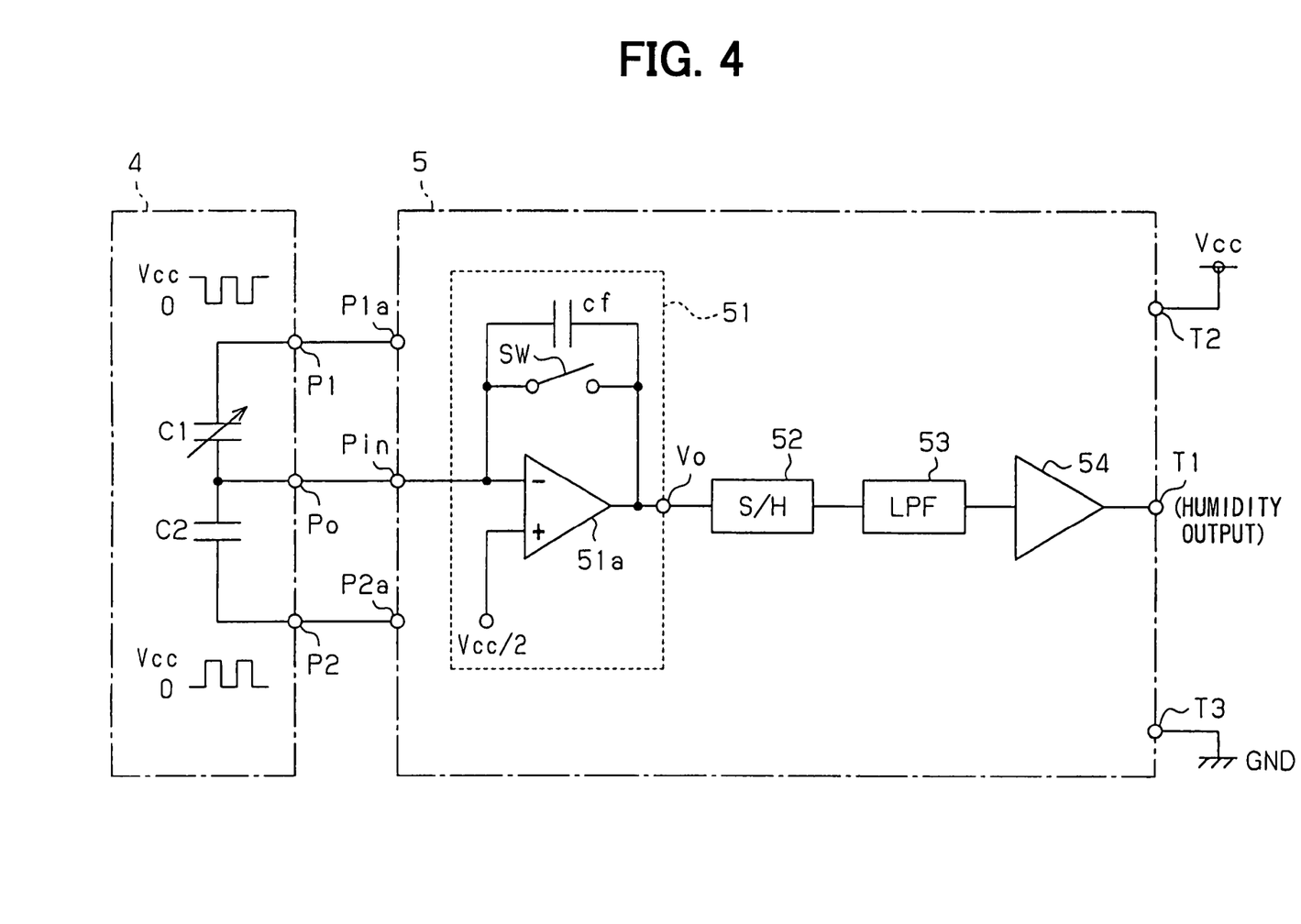
FIG. 4 is a block diagram showing an electrical connection structure of the humidity sensor according to the first embodiment.

As shown in FIG. 4, this humidity sensor includes the humidity sensor chip 4 functioning as the humidity sensor, and the processing circuit chip 5 for electrically processing humidity information obtained from the humidity sensor chip 4. In FIG. 4, the relation of synthetic capacities (electrical capacitances) C1, C2 of the humidity sensor chip 4 is shown with this humidity sensor chip 4 as an equivalent circuit. Further, the processing circuit chip 5 is constructed with a switched capacitor circuit 51, a sample and hold circuit (S/H) 52, a low pass filter (LPF) 53, an amplifier 54, etc.

In this humidity sensor chip 4, the change of the humidity is detected as a change of the electrical capacitance C1, and this change of the electrical capacitance C1 with respect to the fixed electrical capacitance C2 is output from a terminal Po. Further, the processing circuit chip 5 takes-in this change of the electrical capacitance C1 through a terminal Pin, and converts the change of the electrical capacitance C1 from the terminal Po into a voltage Vo through the switched capacitor circuit 51. This switched capacitor circuit 51 is constructed with an arithmetic amplifier 51a, a capacitor (feedback capacitor) cf connected in parallel with a feedback path of the arithmetic amplifier 51a, and a switch SW. A signal taken into the terminal Pin is inputted to an inversion input terminal of the arithmetic amplifier 51a. For example, a voltage half a power source voltage Vcc applied between terminals P1 and P2, i.e., a voltage of "Vcc/2" is given to a non-inversion input terminal of the arithmetic amplifier 51a. Here, Vcc/2 corresponds to a voltage appearing at the terminal Po when the electrical capacitance C1 and the electrical capacitance C2 are equal to each other.

An alternating signal of a predetermined frequency alternated in phases reverse to each other between voltage 0 V and the power source voltage Vcc is formed by an unillustrated pulse generating circuit, etc. within the processing circuit chip 5. This alternating signal is respectively applied from terminals P1a, P2a of the processing circuit chip 5 to the terminals P1, P2 of the humidity sensor chip 4. The above switch SW of the switched capacitor circuit 51 is ON/OFF-controlled in synchronization with an alternating period of each of these alternating signals (voltages). While such an operation is repeated, the voltage Vo converted in C (capacitance)–V (voltage) by the switched capacitor circuit 51 is suitably sample-held by the sample and hold circuit 52. This sampled-held signal is inputted to the low pass filter 53, and its high frequency component is removed. After the output of this low pass filter 53 is gain-adjusted by the amplifier 54, this adjusted signal is externally outputted through a terminal T1 as a signal showing humidity information. In this humidity sensor, the relative humidity is normally calculated together with reference to temperature information using a temperature sensor separately arranged.

In this humidity sensor, as mentioned above, the terminals P1, P2 and the terminal Po of the humidity sensor chip 4 shown in FIG. 4 are wire-bonded to the terminals P1a, P2a and the terminal Pin of the processing circuit chip 5. The respective terminals T1 to T3 shown in FIG. 4, i.e., the terminal T1 for outputting the humidity information, and electricity supply terminals T2, T3 are wire-bonded to the conductor 1 (FIG. 1) as sensor terminals.

Figure 5:
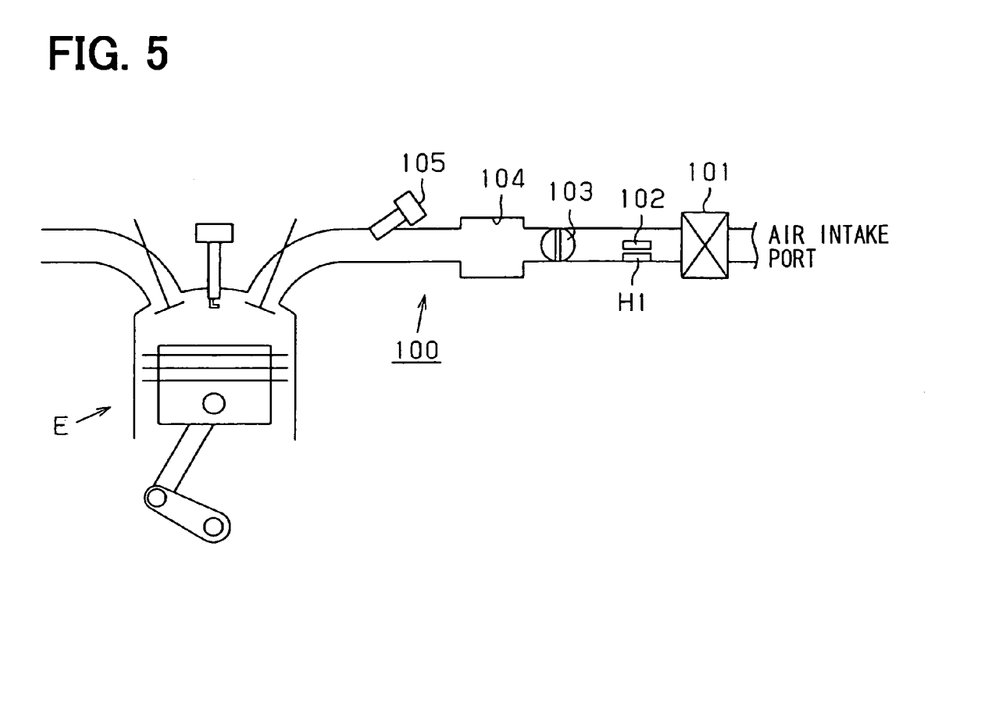
FIG. 5 is a schematic diagram showing an example where the humidity sensor is located in an intake air passage of an engine.

For example, as illustrated in FIG. 5, the humidity sensor according to this embodiment having the structure is arranged in an intake gas passage of the engine, particularly, in the vicinity of an air flow meter, and can be used as a sensor for detecting a humidity component included in the intake air.

In the intake gas passage 100 of the engine E, an air filter 101, an air flow meter 102, a throttle valve 103, a serge tank (intake manifold) 104, an injector 105, etc. are normally arranged from the upstream side of the intake gas passage 100. In the intake gas passage 100 of the engine E, a humidity component included in the intake air supplied to the engine E can be detected by arranging the humidity sensor (for brevity, this humidity sensor is indicated as H1 in FIG. 5) in the vicinity of e.g., the air flow meter 102. A correction according to the detected humidity component with respect to the intake air amount detected by the air flow meter 102 can be performed by detecting this humidity component. Electronic control fuel injection of the engine E can be performed with higher precision because this humidity component can be precisely detected.

In accordance with the humidity sensor according to this embodiment described in detail above, the following effects can be obtained.

In comparison with the surface area of the humidity sensing portion 40a (humidity sensing film 45) of the humidity sensor chip 4, the surface area of the filled protecting material 7 of the humidity sensing property is greatly widened. Therefore, as long as the polluting substance D does not perfectly cover the surface of the filled protecting material 7 of the humidity sensing property even when the above-mentioned polluting substance D is attached to this humidity sensor, moisture enters from a portion except for this covering portion through this protecting material 7 of the humidity sensing property. Thus, no function as this humidity sensor is damaged. That is, a resisting amount with respect to the attachment of the polluting substance D is greatly improved by a difference in the surface area. Further, the distances between the surface of the protecting material 7 having the humidity sensing property and the pair of electrodes 43a, 43b of the humidity sensor chip 4 itself functioning as the humidity sensor are also held to be sufficiently long by the filling of the protecting material 7 of the humidity sensing property. Therefore, even when the dielectric constant of the attached polluting substance D is high, there is no an influence on the electrical capacitance C1 between these electrodes 43a and 43b. The dielectric constant of the filled protecting material 7 of the humidity sensing property is also really changed by humidity absorption, but such a change of the dielectric constant can be obtained as an experience value (experimental value) in advance. Accordingly, this changing amount is easily canceled by subsequent electric processing. To cancel this changing amount, there is a method for storing a map or an arithmetic formula, etc. for canceling this changing amount into an EPROM, etc. in advance within e.g., the processing circuit chip 5, and correcting obtained humidity information by this map or arithmetic formula.

For example, a drug resisting property can be suitably secured in the humidity sensor by adopting the fluorine gel as the protecting material 7 having the humidity sensing property.

The electronic control fuel injection of the engine E can be performed with higher precision by arranging this humidity sensor H1 within the intake gas passage 100 of the engine E, particularly, in the vicinity of the air flow meter 102, and using this humidity sensor for detecting the humidity component included in the intake air supplied to this engine E.

For example, the above-described embodiment can be also executed as the following mode for suitably changing this embodiment.

In the above-described embodiment, two kinds of chips constructed with the humidity sensor chip 4 and the processing circuit chip 5 are used, but a construction for integrating the humidity sensor chip 4 and the processing circuit chip 5 into one chip may be also used.

In the above-described embodiment, the fluorine gel is typically used as the protecting material 7 having the humidity sensing property, but the protecting material 7 having the humidity sensing property is not limited to such a material. For example, gel such as silicon gel, fluoro silicon gel, etc. can be also adopted as the protecting material 7 having the humidity sensing property.

In the above-described embodiment, only one humidity sensor chip 4 functioning as the humidity sensor is used, but a construction for arranging plural humidity sensor chips 4 and electrically synthesis-processing humidity information obtained from each of these humidity sensor chips as the processing circuit chip 5 may be also used. In accordance with such a construction, it is possible to perform the humidity detection with a higher reliability by utilizing a wide surface area of the filled protecting material 7.

Figure 6:
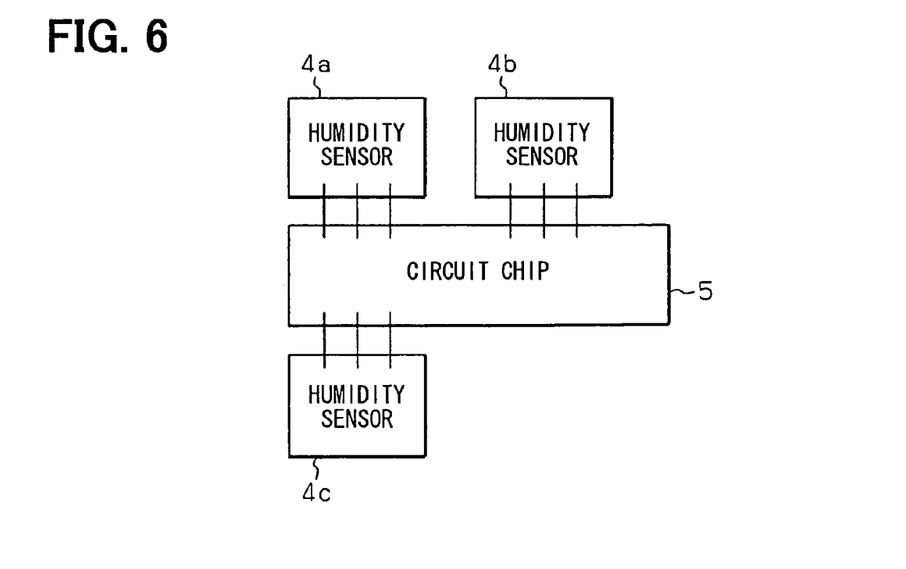
FIG. 6 is a block diagram showing a humidity sensor according to a modification of the first embodiment.

For example, as shown in FIG. 6, the humidity sensor chip functioning as the humidity sensor may be constructed with three humidity sensor chips 4a, 4b, 4c, and the humidity information using each of these humidity sensor chips 4a, 4b, 4c may be also processed by majority decision through the processing circuit chip 5. Thus, the reliability of the humidity sensor can be effectively improved. When such processing using the decision by majority is performed, the number of humidity sensor chips may be set to an odd number of three or more.

Figure 7:
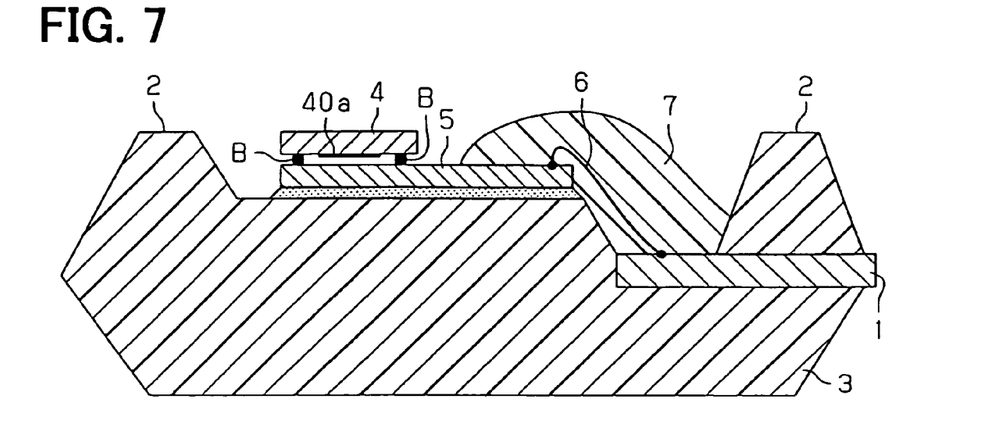
FIG. 7 is a cross-sectional view showing a humidity sensor according to another modification of the first embodiment.

Further, arrangement states of the humidity sensor chip 4 and the protecting material 7 having the humidity sensing property are also not limited to the states in the above-described embodiment. For example, as shown in FIG. 7, a flip chip structure having a metallic bump B such as a solder bump, a gold bump, etc. is used as the humidity sensor chip 4. A structure in which the humidity sensing portion 40a as a humidity detecting portion is arranged on the arranging side of the metallic bump B can be used. The humidity sensor chip 4 functioning as this humidity sensor can be mounted onto the surface of the processing circuit chip by electrically connecting the humidity sensor chip 4 to the processing circuit chip 5 using this metallic bump B. In this case, the humidity sensing portion 40a itself of the humidity sensor chip 4 is originally protected from the attachment of the polluting substance D. Therefore, no function as the humidity sensor is also damaged in this case.

Figure 8:
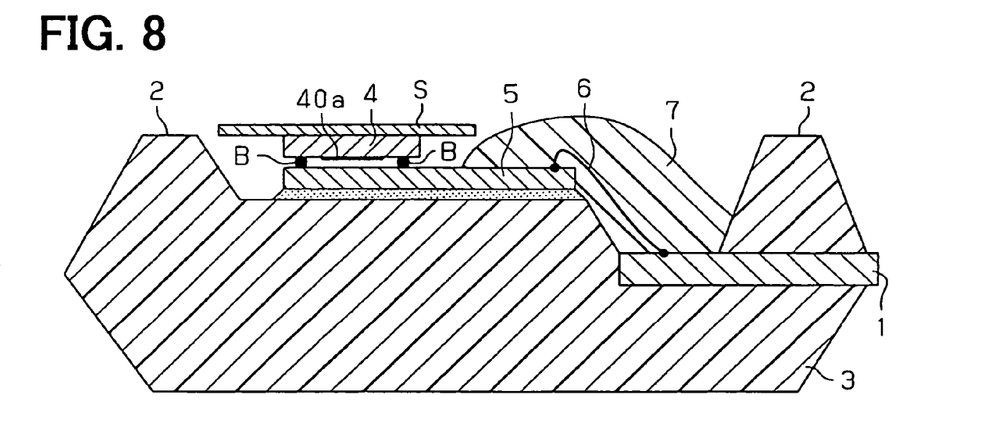
FIG. 8 is a cross-sectional view showing a humidity sensor according to another modification of the first embodiment.

Alternatively, as shown in FIG. 8, a shield plate S for covering the circumference of the humidity sensor chip 4 and this humidity sensor chip 4 is further arranged on the back surface of the mounting surface of the humidity sensor chip 4 having the flip chip structure with respect to the processing circuit chip 5.

Figure 9:
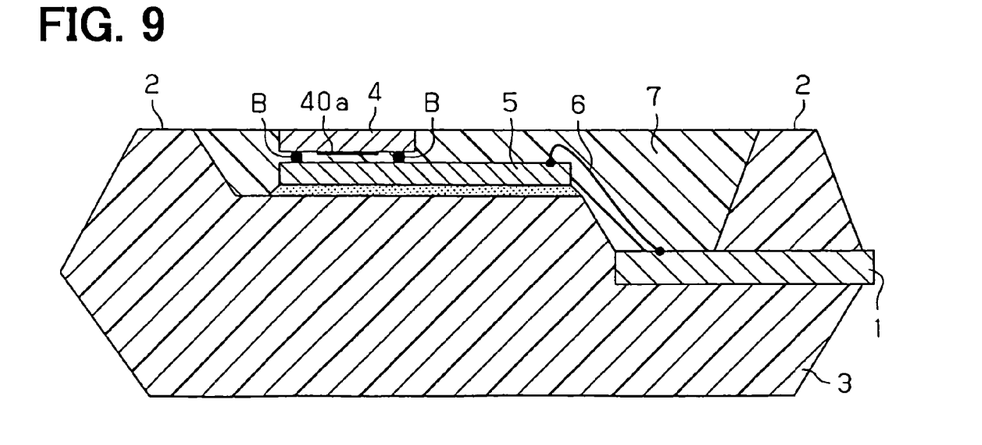
FIG. 9 is a cross-sectional view showing a humidity sensor according to another modification of the first embodiment.

Alternatively, as shown in FIG. 9, an entire portion including an electric connecting portion of the humidity sensor chip 4 and the processing circuit chip 5 having the flip chip structure is covered with the protecting material 7 having the humidity sensing property. In this case, the protecting material 7 is filled in the wall portion 2 to cover the entire portion of the humidity sensor chip 4 and the processing circuit chip 5, including the electric connecting portion therebetween.

Accordingly, the protecting function with respect to the adhering of the polluting substance D is further promoted, and reliability and precision as the humidity sensor are further raised. The material of the shield plate S can be arbitrarily selected, and for example, a material made of a resin or a metal can be used as the material of the shield plate S.

Second Embodiment

Figure 10A:
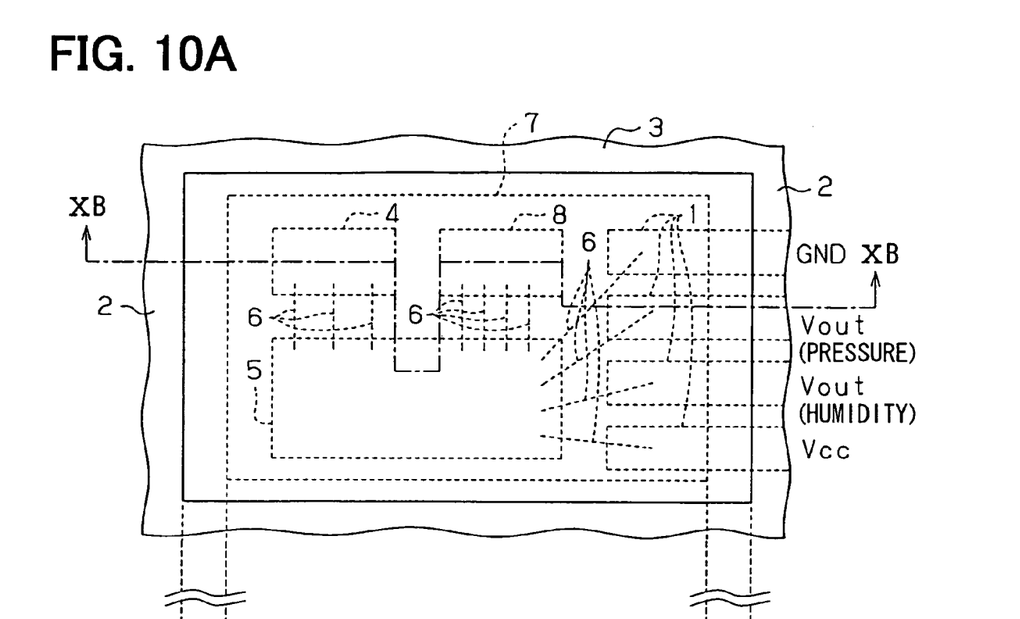
FIG. 10A is a plan view showing a composite sensor having a humidity detecting function according to a second embodiment of the present invention.
Figure 10B:
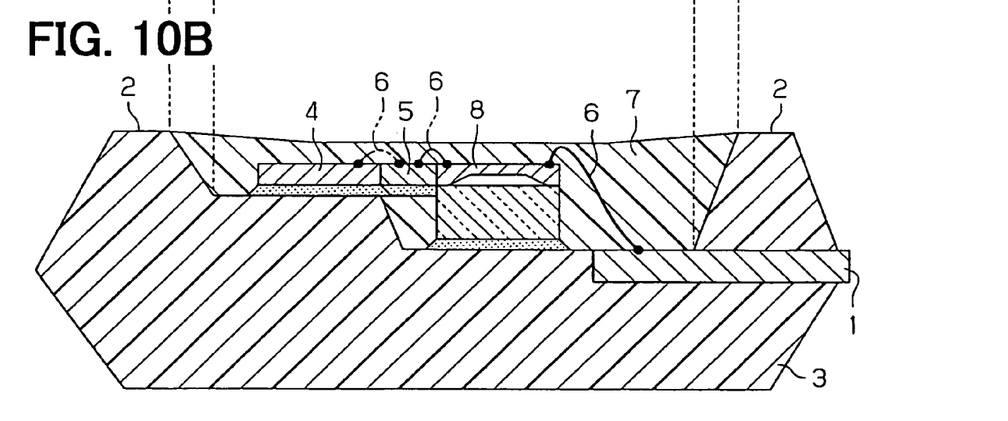
FIG. 10B is a cross-sectional view showing the composite sensor taken along line XB—XB in FIG. 10A.

As shown in FIGS. 10A and 10B, a composite sensor having a humidity detecting function is insert-molded to a resin molding body 3 having a wall portion 2 as a barrage in the circumference such that conductors 1 (terminal conductors) as sensor terminals are partially guided to the exterior. A humidity sensor chip 4 functioning as a humidity sensor, a well-known pressure sensor chip 8 using e.g., distortion resistance, etc. and functioning as a pressure sensor, and a processing circuit chip 5 for electrically processing humidity and pressure information obtained from both the sensor chips 4, 8 are separately integrated, bonded and fixed to an intermediate portion of this resin molding body 3.

Further, both the sensor chips 4, 8, the processing circuit chip 5 and the conductors 1, which are adhered and fixed, are electrically connected through bonding wires 6 inside the wall portion 2 of the resin molding body 3. The entire electric connecting portion including this bonding wires 6 is covered with the protecting material 7 having the humidity sensing property. The protecting material 7 is filled in the wall portion 2.

Figure 11:
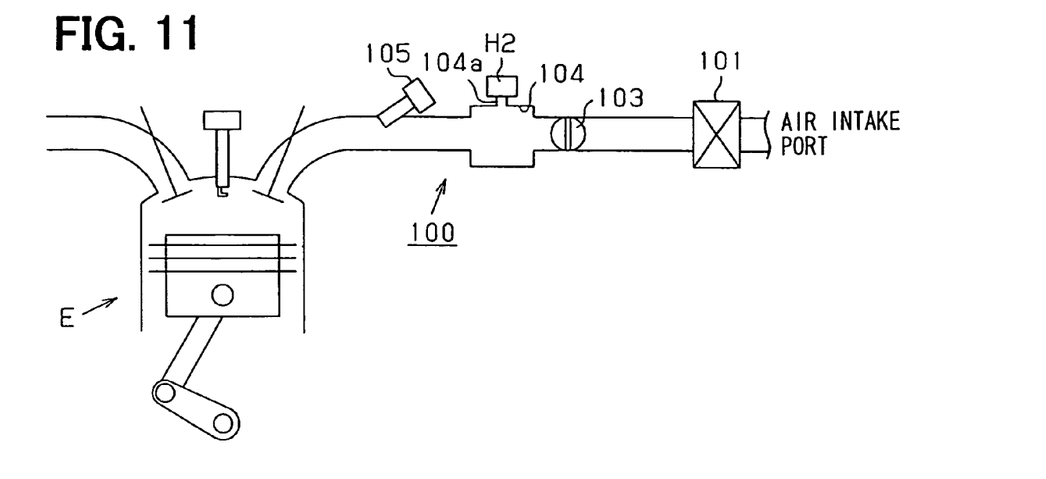
FIG. 11 is a schematic diagram showing an example where the composite sensor is located in an intake air passage of an engine.

For example, as shown in FIG. 11, a composite sensor H2 having the humidity detecting function according to this embodiment can be arranged in an intake gas passage of an engine, particularly, in the vicinity of an intake manifold gathering portion (serge tank), and can be used as a sensor for detecting a humidity component included in the intake air together with the internal pressure of an intake gas pipe. For example, as shown in FIG. 11, the intake gas passage 100 of the engine E includes an air filter 101, a throttle valve 103, a serge tank 104, an injector 105, etc. from the upstream side of this intake gas passage 100. In this case, the composite sensor H2 is arranged in the serge tank 104. More concretely, this composite sensor H2 is arranged through a pressure introducing pipe 104*a* guided from this serge tank 104. Thus, it is possible to detect the humidity component included in the intake air, together with the internal pressure of the intake gas pipe of the engine E. In particular, similar to the above description, the electronic control fuel injection of the engine E can be performed with higher precision by correcting the value of the internal pressure of the intake gas pipe on the basis of this detected humidity component. Here, the value of the internal pressure of the intake gas pipe is a value corresponding to the previous intake air amount in the intake gas pipe.

Because the humidity sensor chip 4 is provided in the composite sensor, the advantage described in the first embodiment can be obtained.

Furthermore, in accordance with this embodiment, in comparison with the surface areas of the humidity sensor chip 4 and the pressure sensor chip 8, the surface area of the filled protecting material 7 having the humidity sensing property and a pressure sensing property is greatly widened. Therefore, in this case, as long as no polluting substance D perfectly covers the surface of the filled protecting material 7 even when the above-described polluting substance D is attached to this composite sensor, moisture enters from a portion except for this covering portion through this protecting material 7. Accordingly, no function in the composite sensor having at least the humidity detecting function is damaged. Furthermore, such a structure is also effective as a protecting structure of the pressure sensor chip 8 functioning as a well-known pressure sensor. With respect to the pollution of a pressure sensing portion of a portion functioning as the pressure sensor, its influence can be suitably avoided.

The electronic control fuel injection of the engine E can be performed with higher precision by arranging the composite sensor within the intake gas passage 100 of the engine E, particularly, in the serge tank (intake manifold) 104 through the pressure introducing pipe 104*a*, and using the composite sensor for detecting the humidity component of the intake air together with the internal pressure of the intake gas pipe.

Other Embodiments

Although the present invention has been described in connection with some embodiments thereof with reference to the accompanying drawings, it is to be noted that various changes and modifications will become apparent to those skilled in the art.

For example, in the above-described second embodiment, the three-chip construction of the humidity sensor chip 4, the pressure sensor chip 8 and the processing circuit chip 5 is illustrated as a chip structure. However, the chip structure is not limited to such a three-chip structure. For example, the following arbitrary chip structures, etc. may be used as a chip adhering and fixed to the inside of the wall portion 2 of the resin molding body 3 and may be electrically connected to the conductors 1.

As an example, a single chip may be used as the chip structure (chip member) by integrally integrating a portion functioning as the humidity sensor, a portion functioning as the pressure sensor, and a processing circuit for electrically processing detection information from these portions.

Alternatively, the chip structure (chip member) can be constructed by using two chips. For example, the chip structure can be constructed with a chip formed by integrating a portion functioning as the humidity sensor and a portion functioning as the pressure sensor, and the processing circuit chip 5 for electrically processing detection information of these portions.

Further, the chip structure can be constructed with the humidity sensor chip 4 functioning as the humidity sensor, and the processing circuit chip 5. In this case, the processing circuit chip 5 has a portion functioning as the pressure sensor and electrically processes detection information using this portion and detection information obtained from the humidity sensor chip 4 functioning as the humidity sensor.

Further, the chip structure can be constructed with the pressure sensor chip 8 functioning as the pressure sensor, and the processing circuit chip 5. In this case, the processing circuit chip 5 has a portion functioning as the humidity sensor and electrically processes detection information using this portion and detection information obtained from the pressure sensor chip 8 functioning as the pressure sensor.

Figure 12:
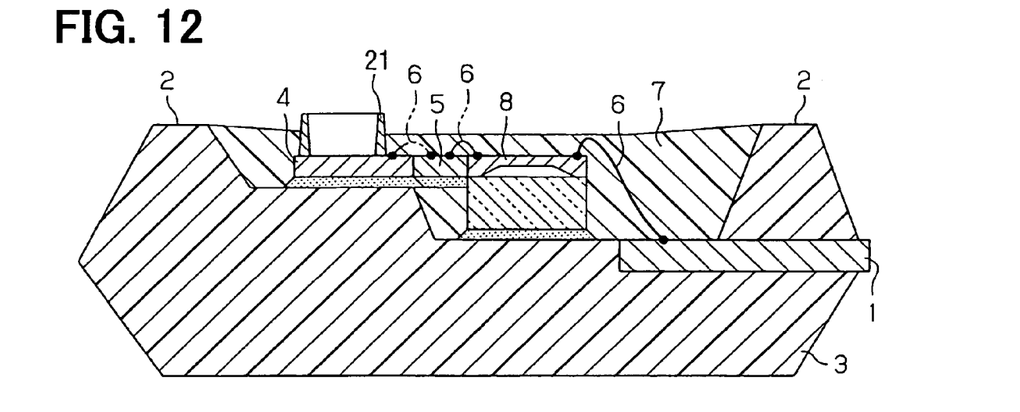
FIG. 12 is a cross-sectional view showing a composite sensor according to a modification of the second embodiment.

Further, as shown in FIG. 12, the adhered and fixed chip and the conductors 1 can be electrically connected inside the wall portion 2 of the resin molding body 3, and the electric connecting portions of the adhered and fixed chip and the conductors 1 can be covered with the protecting material 7 having the humidity sensing property and the pressure sensing property filled in the wall portion 2 as a barrage. Further, at least the humidity sensor chip 4 functioning as the humidity sensor can be independently arranged as the chip adhered and fixed to the inside of the wall portion 2 of the resin molding body 3, and the circumference of the humidity sensing portion 40*a* of the humidity sensor chip 4 functioning as the humidity sensor can be surrounded by a wall material 21 (separation wall) higher than the wall portion 2 of the resin molding body 3. A structure for selectively isolating the humidity sensing portion 40*a* of the humidity sensor chip 4 functioning as the humidity sensor from the protecting material 7 filled in the wall portion 2 of the resin molding body 3 can be formed using the wall material 21 as a barrage. In accordance with such a structure as the composite sensor having the humidity detecting function, responsibility of the humidity sensing portion 40*a* is reliably increased although a slight risk due to the exposure of the humidity sensing portion 40*a* of the humidity sensor chip 4 is caused.

Figure 13:
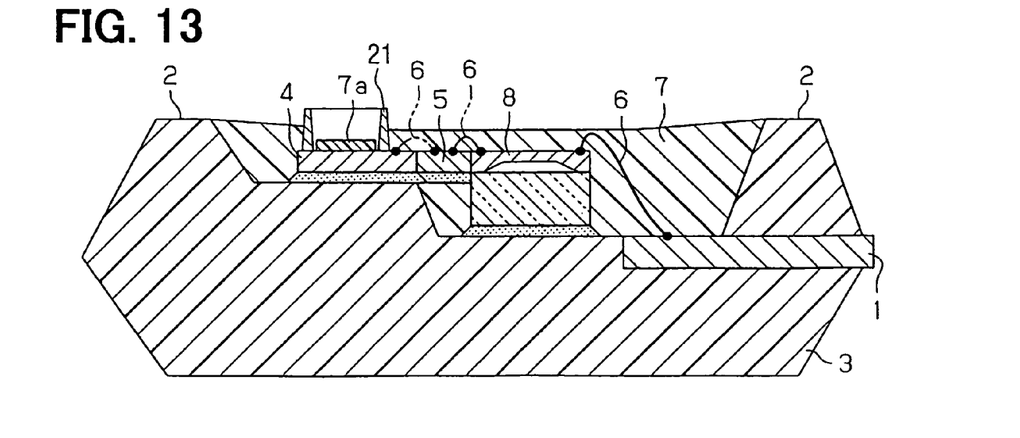
FIG. 13 is a cross-sectional view showing a composite sensor according to another modification of the second embodiment.

Furthermore, as shown in FIG. 13, the humidity sensing portion 40a of the humidity sensor chip 4 functioning as the humidity sensor may be isolated from the protecting material 7 filled in the wall portion 2 of the resin molding body 3. In this case, it is also possible to set a structure for separately forming a protecting film 7a having the humidity sensing property to be different in characteristics from the filled protecting material 7, and to be thinner than this protecting material 7. In accordance with this structure, the risk can be restricted and responsibility and reliability can be suitably improved.

Figure 14A:
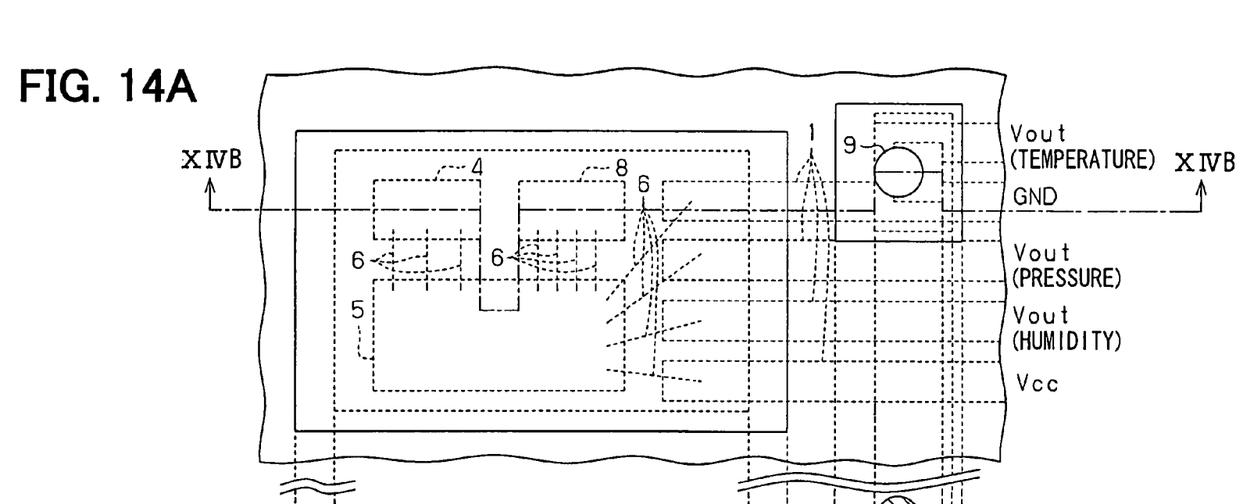
FIG. 14A is a plan view showing a composite sensor having a humidity detecting function according to another modification of the second embodiment.
Figure 14B:
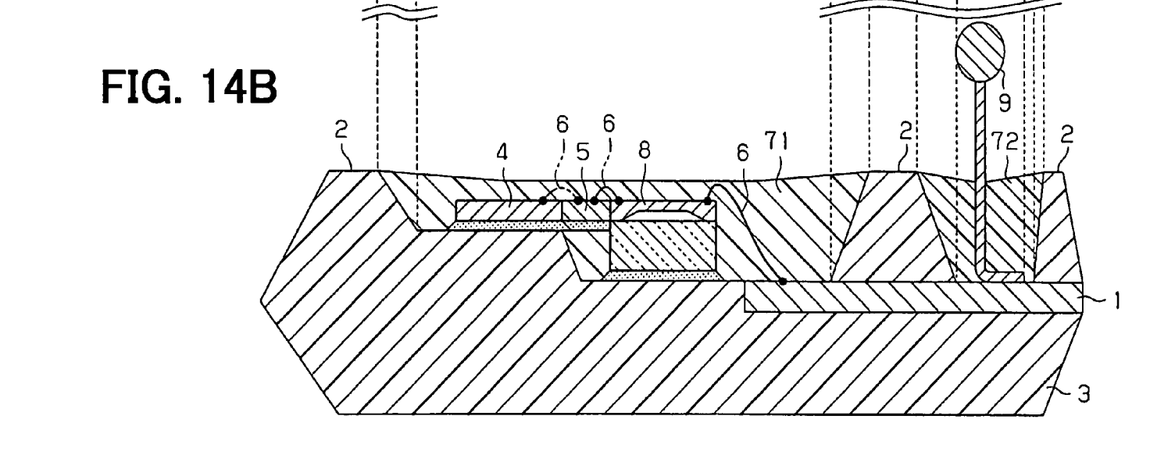
FIG. 14B is a cross-sectional view showing the composite sensor taken along line XIVB—XIVB in FIG. 14A.

As the composite sensor having the humidity detecting function, it is also possible to set a structure having an element 9 (e.g., thermistor) functioning as a temperature sensor outside the wall portion 2 of the resin molding body 3, as shown in FIG. 14. In this case, the relative humidity can be also easily detected using a single sensor (composite sensor).

In such a composite sensor, it may be possible to similarly adopt the previous structure illustrated in FIGS. 5 to 9 with respect to the humidity detecting portion of the composite sensor.

Further, the use for arranging these sensors in the intake gas passage of the engine including the previous humidity sensor (first embodiment) has been illustrated, but this use is arbitrary. This invention can be applied to all sensors for performing the humidity detection with higher precision under the deteriorated environment particularly described before.

While the invention has been described with reference to preferred embodiments thereof, it is to be understood that the invention is not limited to the preferred embodiments and constructions. The invention is intended to cover various modification and equivalent arrangements. In addition, while the various elements of the preferred embodiments are shown in various combinations and configurations, which are preferred, other combinations and configuration, including more, less or only a single element, are also within the spirit and scope of the invention.

What is claimed is:

1. A humidity sensor comprising:
   a resin molding body having a wall portion as a barrage;
   a chip member having at least a humidity sensing function, the chip member adhering and fixed to a portion of the resin molding body, inside the wall portion;
   a terminal conductor insert-molded in the resin molding body and partially leaded to an exterior of the resin molding body, wherein the terminal conductor is electrically connected to the chip member inside the wall portion of the resin molding body; and
   a protecting material having a humidity sensing property, which is filled in the wall portion and covers an entire electric connecting portion of the chip member and the terminal conductor.

2. The humidity sensor according to claim 1, wherein the chip member is constructed with one of a single chip that is formed by integrally integrating a humidity sensing portion having the humidity sensing function and a processing circuit for electrically processing humidity information from the humidity sensing portion, and a plurality of chips formed by separately integrating a chip having the humidity sensing portion and a processing circuit chip for electrically processing humidity information from the chip having the humidity sensing portion.

3. The humidity sensor according to claim 1, wherein:
   the chip member is constructed with a plurality of chips functioning as the humidity sensing portion, and a processing circuit chip for electrically synthesis-processing humidity information from each of the chips; and
   the chips are integrated separately from the processing circuit chip.

4. The humidity sensor according to claim 3, wherein the chips functioning as the humidity sensing portion are constructed with odd chips of three or more than three, and the processing circuit chip processes the humidity information using signals from the chips by a majority decision.

5. The humidity sensor according to claim 1, wherein the protecting material covers all of the chip member and the electric connecting portion.

6. A humidity sensor comprising:
   a resin molding body having a wall portion as a barrage;
   a chip having at least a humidity sensing function;
   a processing circuit chip for electrically processing humidity information from the chip having the humidity sensing function, wherein the processing circuit chip adhering and fixed to a portion of the resin molding body, inside the wall portion;
   a terminal conductor insert-molded in the resin molding body and partially leaded to an exterior of the resin molding body, wherein the terminal conductor is electrically connected to the processing circuit chip inside the wall portion of the resin molding body; and
   a protecting material having a humidity sensing property, which is filled in the wall portion and covers an entire electric connecting portion of the processing circuit chip and the terminal conductor, wherein:
   the chip having the humidity sensing function is constructed with a flip chip having a metallic bump, and has a humidity sensing portion arranged on an arrangement surface where the metallic bump is provided; and
   the chip having the humidity sensing function is electrically connected to the processing circuit chip by the metallic bump, and is attached to the processing circuit chip through the electrical connection.

7. The humidity sensor according to claim 6, further comprising
   a shield plate which covers the chip having the humidity sensing function and a circumference of the chip, on a surface opposite to the arrangement surface of the chip having the humidity sensing function.

8. The humidity sensor according to claim 6, wherein the protecting material filled in the wall portion covers an entire area including the chip having the humidity sensing function, the processing circuit chip, and the electric connecting portion of the chip having the humidity sensing function and the processing circuit chip.

9. The humidity sensor according to claim 1, wherein the protecting material is made of gel.

10. The humidity sensor according to claim 9, wherein the gel is composed of fluorine gel.

11. The humidity sensor according to claim 1, wherein the chip member fixed to the resin molding body is mounted in an intake gas system of an engine for a vehicle, and detects a humidity component in intake air supplied to the engine.

12. A composite sensor comprising:
   a resin molding body having a wall portion as a barrage;
   a chip member having at least a humidity sensing function and a pressure sensing function, the chip member adhering and fixed to a portion of the resin molding body, inside the wall portion;
   a terminal conductor insert-molded in the resin molding body and partially leaded to an exterior of the resin molding body, wherein the terminal conductor is electrically connected to the chip member inside the wall portion of the resin molding body; and a protecting material having a humidity sensing property and a pressure sensing property, which is filled in the wall portion and covers an entire electric connecting portion of the chip member and the terminal conductor.

13. The composite sensor according to claim 12, wherein the chip member is constructed with a single chip that is formed by integrally integrating a humidity sensing portion having the humidity sensing function, a pressure sensing portion having the pressure sensing function, and a processing circuit for electrically processing humidity information from the humidity sensing portion and pressure information from the pressure sensing portion.

14. The composite sensor according to claim 12, wherein the chip member is constructed with a chip in which a humidity sensing portion having the humidity sensing function and a pressure sensing portion having the pressure sensing function are integrated, and a processing circuit chip for electrically processing information from the chip having the humidity sensing portion and the pressure sensing portion.

15. The composite sensor according to claim 12, wherein:
the chip member is constructed with a chip having the humidity sensing function, and a processing circuit chip including a pressure sensing portion having the pressure sensing function; and
the processing circuit chip electrically processes information from the chip having the humidity sensing function and information from the pressure sensing portion.

16. The composite sensor according to claim 12, wherein:
the chip member is constructed with a chip having the pressure sensing function, and a processing circuit chip including a humidity sensing portion having the humidity sensing function; and
the processing circuit chip electrically processes information from the chip having the pressure sensing function and information from the humidity sensing portion.

17. The composite sensor according to claim 12, wherein:
the chip member is constructed with a chip having the humidity sensing function, a chip having the pressure sensing function, and a processing circuit chip for electrically processing information from the chip having the pressure sensing function and information from the chip having the humidity sensing function.

18. A composite sensor comprising:
a resin molding body having a wall portion as a barrage;
a humidity chip having at least a humidity sensing function, adhering and fixed to a portion of the resin molding body inside the wall portion;
a pressure chip having at least a pressure sensing function, adhering and fixed to a portion of the resin molding body inside the wall portion;
a terminal conductor insert-molded in the resin molding body and partially leaded to an exterior of the resin molding body, wherein the terminal conductor is electrically connected to the humidity chip and the pressure chip inside the wall portion of the resin molding body; and a protecting material having a humidity sensing property and pressure sensing property, which is filled in the wall portion and covers an entire electric connecting portion of the chips and the terminal conductor, wherein:
at least the humidity chip is provided independently and has a humidity sensing portion for detecting humidity;
the humidity sensing portion of the humidity chip is enclosed by a separation wall that is higher than the wall portion of the resin molding body; and
the separation wall selectively separates the humidity sensing portion from the protecting material filled in the wall portion of the resin molding body.

19. The composite sensor according to claim 18, further comprising
a protecting film having a thickness thinner than the thickness of the protecting material, wherein the protecting film covers the humidity sensing portion separated from the protecting material.

20. The composite sensor according to claim 12, further comprising
a temperature detecting element located at an outer side of the wall portion of the resin molding body.

21. The composite sensor according to claim 12, wherein the protecting material is made of gel.

22. The composite sensor according to claim 12, wherein the gel is composed of fluorine gel.

23. The composite sensor according to claim 12, wherein the chip member fixed to the resin molding body is mounted in an intake gas system of an engine for a vehicle, and detects a humidity component and a pressure in intake air supplied to the engine.

24. The composite sensor according to claim 18, further comprising
a temperature detecting element located at an outer side of the wall portion of the resin molding body.

25. The composite sensor according to claim 18, wherein the protecting material is made of gel.

26. The composite sensor according to claim 18, wherein the gel is composed of fluorine gel.

27. The composite sensor according to claim 18, wherein the humidity chip and the pressure chip fixed to the resin molding body are mounted in an intake gas system of an engine for a vehicle, and detects a humidity component and a pressure in intake air supplied to the engine.

* * * * *